(12) United States Patent
Marshall

(10) Patent No.: US 10,968,162 B2
(45) Date of Patent: Apr. 6, 2021

(54) METHOD FOR THE SYNTHESIS AND PURIFICATION OF ARYL ACID ESTERS

(71) Applicant: Miami University, Oxford, OH (US)

(72) Inventor: Janet Marshall, Middletown, OH (US)

(73) Assignee: Miami University, Oxford, OH (US)

( * ) Notice: Subject to any disclaimer, the term of this patent is extended or adjusted under 35 U.S.C. 154(b) by 0 days.

(21) Appl. No.: 16/369,583

(22) Filed: Mar. 29, 2019

(65) Prior Publication Data

US 2019/0300471 A1 Oct. 3, 2019

Related U.S. Application Data

(60) Provisional application No. 62/650,494, filed on Mar. 30, 2018.

(51) Int. Cl.
*C07C 67/58* (2006.01)
*C07C 67/52* (2006.01)

(52) U.S. Cl.
CPC .............. *C07C 67/58* (2013.01); *C07C 67/52* (2013.01)

(58) Field of Classification Search
CPC ....... C07C 67/52; C07C 67/08; C07C 201/12; C07C 69/65; C07C 69/734; C07C 69/76; C07C 69/92; C07C 205/56; C07C 205/57; C07C 67/58; C07C 201/00

See application file for complete search history.

(56) References Cited

FOREIGN PATENT DOCUMENTS

| CN | 105218322 | * | 1/2016 |
| WO | WO2017/204913 | * | 11/2017 |

OTHER PUBLICATIONS

CN105218322 (Year: 2016).*

* cited by examiner

*Primary Examiner* — Jafar F Parsa
*Assistant Examiner* — Blaine G Doletski
(74) *Attorney, Agent, or Firm* — Calfee, Halter & Griswold, LLP

(57) ABSTRACT

The general inventive concepts are directed to the discovery that certain aryl acids can be esterified under particular conditions to provide the resulting ester as a solid that precipitates in good yield from the reaction mixture. The esters may then be isolated and purified with relative ease. Accordingly, a method for the esterification, isolation, and purification of aryl acids is provided.

11 Claims, No Drawings

METHOD FOR THE SYNTHESIS AND PURIFICATION OF ARYL ACID ESTERS

RELATED APPLICATIONS

This non-provisional application claims the benefit of U.S. provisional application No. 62/650,494, filed Mar. 30, 2018, the content of which is hereby incorporated by reference.

FIELD

The general inventive concepts described herein relate to chemical synthesis and purification and, more particularly, to improved methods for the esterification of aryl acids.

BACKGROUND

Benzoic and cinnamic acid esters and related structures are well-known and versatile chemical intermediates that are widely used in a variety of industries. The multiple chemical functionalities present in the molecules, coupled with their relative abundance makes them attractive targets for the manufacture of more complex chemical structures. Currently, cinnamic acid esters and similar chemical species are important intermediates in perfume science, agricultural chemicals, and pharmaceuticals, among others.

Cinnamic acid esters can be produced through, oxidative carboxylation of styrenes in the presence of an alcohol, reaction of a benzaldehyde with an acetic acid ester, or through esterification of the cinnamic acid itself. One well-known method for esterification of aryl acids is the so-called Fischer esterification. In general, this process involves dissolving the aryl acid in the desired alcohol and heating the solution in the presence of a strong acid (e.g., sulfuric acid). The alcohol solvent thus also is a reactant. In general, once the reaction is complete, the ester is isolated from the reaction mixture by the desired purification method, often chromatography. The general methods for production of cinnamic acid esters suffer from one or more common drawbacks such as expensive catalysts, lengthy purification, or large amounts of waste or unwanted by-products. Due to the broad desire for aryl acid esters, there is a need for an improved method for the production and purification of cinnamic acid esters, one which preferably address one or more of the aforementioned drawbacks.

SUMMARY

The general inventive concepts discussed herein are based, at least in part, on the discovery that certain aryl carboxylic acids undergo acid-catalyzed esterification in relatively concentrated reaction mixtures and the resulting aryl ester precipitates from the reaction mixture, allowing for improved/easier purification and isolation of the ester.

The general inventive concepts thus provide a process for the esterification of aryl acids via heating the acid in an alcohol solvent in the presence of an acid catalyst. The inventive methods provide the resulting ester in good yield with excellent purity while avoiding the time, waste, and cost associated with purification necessary after conventional esterification processes.

In general, the inventive method provides for esterification of aryl acids according to formula I:

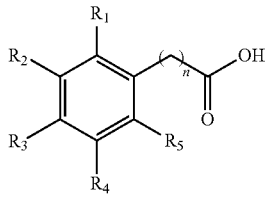

In an exemplary embodiment, a method for the synthesis of an aryl ester of formula II is provided.

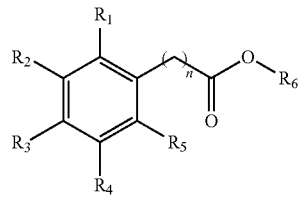

Formula II

The method comprises mixing an aryl acid according to formula I, with an alcohol solvent and an acid catalyst to form a reaction mixture.

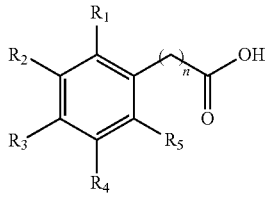

Formula I http://patentimages.storage.googleapis.com/EP0909751B1/00020001.png

Heating the reaction mixture for a period of 0.5 to 10 hours, filtering the reaction mixture and washing the aryl ester with a solvent. Wherein the molar ratio of aryl acid to alcohol solvent is 1:100 to 1:5. Wherein the molar ratio of aryl acid:acid catalyst in a molar ratio of from 1:0.5 to 1:0.01. Wherein $R_1$, $R_2$, $R_3$, $R_4$, and $R_5$ each independently represents a hydrogen atom, an alkyl group having from 1 to 6 carbon atoms, a cycloalkyl group having from 3 to 6 carbon atoms, a halogen atom, an alkoxy group having from 1 to 6 carbon atoms, a haloalkyl group having from 1 to 6 carbon atoms, a haloalkoxy group having from 1 to 6 carbon atoms, an alkylthio group having from 1 to 6 carbon atoms, an alkylsulphonyl group having from 1 to 6 carbon atoms, a nitro group, a hydroxy group, a cyano group, a phenyl group, a phenoxy group, an amino group, an alkylamino group having from 1 to 6 carbon atoms or a dialkylamino group having from 1 to 6 carbon atoms in each alkyl part; and n is equal to 0 (i.e., a benzoic acid) or an alkyl group having from 1 to 6 carbon atoms. In certain embodiments, n is equal to —CH═CH— (i.e., a cinnamic acid). Wherein $R_6$ represents an alkyl group having from 1 to 6 carbon atoms or a cycloalkyl group having from 3 to 6 carbon atoms.

Numerous other aspects, advantages, and/or features of the general inventive concepts will become more readily apparent from the following detailed description of exemplary embodiments and from the accompanying drawings.

DETAILED DESCRIPTION

Several illustrative embodiments will be described in detail to provide a better understanding of the invention.

Fischer esterification is a well-known method for esterifying acids. Generally, a carboxylic acid is heated (often to reflux) in an alcohol solvent in the presence of an acid catalyst. The alcohol solvent also serves as the other reactant for formation of the ester group. An example of the reaction is shown below illustrating the reaction of 4-bromocinnamic acid and methanol.

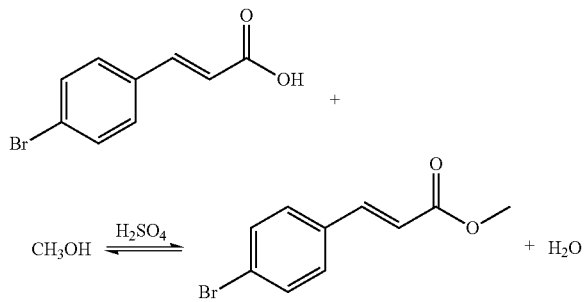

Generally speaking, organic chemical reactions take place in solution. That is, the general aim of an ordinary artisan is for a given reaction mixture to be a solution. In the case of Fischer esterification, it would thus be desirable for the acid to be soluble in the alcohol solvent/reactant. The desirability of solution chemistry is many-fold. Once in solution, the reaction may be heated uniformly, ensuring that the mixture has no "hot" or "cold" spots, ensuring more-complete reaction and a reduction in possible unwanted by-products. Likewise, solution chemistry is widely assumed to allow for greater molecular movement and mixing of reactants. Most often, when presented with a reaction that has not achieved a solution, the ordinary artisan adds additional solvent until the reaction achieves a uniform solution. Further, in circumstances like Fischer-type esterification, where the solvent is also a reactant, the general belief is that adding more solvent to the reaction should also accelerate reaction time, per Le Chatelier's principle (i.e., increasing the concentration of a reactant will cause the reaction to adjust toward the products, speeding up the time to completion).

With this background in mind, the general inventive concepts relate to methods for the synthesis of an aryl ester. More particularly, the general inventive concepts provide methods of esterifying aryl acids and purifying the resulting aryl ester.

In an exemplary embodiment, a method for the synthesis of an aryl ester of formula II is provided.

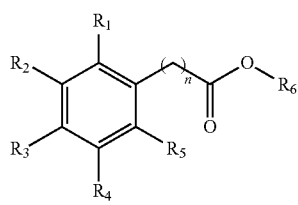

Formula II

The method comprises mixing an aryl acid according to formula I, with an alcohol solvent and an acid catalyst to form a reaction mixture.

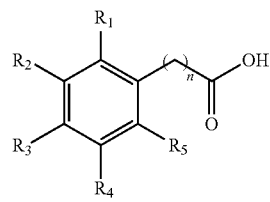

Formula I http://patentimages.storage.googleapis.com/EP0909751B1/00020001.png

Heating the reaction mixture for a period of 0.5 to 10 hours, filtering the reaction mixture and washing the aryl ester with a solvent. Wherein the molar ratio of aryl acid to alcohol solvent is 1:100 to 1:5. Wherein the molar ratio of aryl acid:acid catalyst in a molar ratio of from 1:0.5 to 1:0.01. Wherein $R_1$, $R_2$, $R_3$, $R_4$, and $R_5$ each independently represents a hydrogen atom, an alkyl group having from 1 to 6 carbon atoms, a cycloalkyl group having from 3 to 6 carbon atoms, a halogen atom, an alkoxy group having from 1 to 6 carbon atoms, a haloalkyl group having from 1 to 6 carbon atoms, a haloalkoxy group having from 1 to 6 carbon atoms, an alkylthio group having from 1 to 6 carbon atoms, an alkylsulphonyl group having from 1 to 6 carbon atoms, a nitro group, a hydroxy group, a cyano group, a phenyl group, a phenoxy group, an amino group, an alkylamino group having from 1 to 6 carbon atoms or a dialkylamino group having from 1 to 6 carbon atoms in each alkyl part; and n is equal to 0 (i.e., a benzoic acid) or to an alkyl group having from 1 to 6 carbon atoms. In certain embodiments, n is equal to —CH=CH— (i.e., a cinnamic acid). Wherein $R_6$ represents an alkyl group having from 1 to 6 carbon atoms or a cycloalkyl group having from 3 to 6 carbon atoms.

The inventive concepts are based, at least in part, on the discovery that when certain aryl acids are heated in an alcohol solvent with an acid catalyst, they react to form an aryl ester which precipitates from the reaction mixture.

One of the major advantages of the inventive process is the ability to obtain pure solid esters directly from the reaction mixture with minimal work-up and/or purification. Upon cooling of the reaction, crystalline product precipitates from solution. These highly pure solids are simply filtered, washed with the alcohol solvent or an alcohol/water mix, and dried. The direct crystallization of these esters avoids multi-step purification procedures, such as extraction, chromatography, or recrystallization.

Moreover, the inventive method follows the practices of green chemistry with high atom economy, a safe by-product ($H_2O$), and the potential to recycle the reaction mixture. For example, the reaction of 4-methylcinnamic acid with methanol at a 1:20 molar ratio yields 40% precipitated product. In addition to achieving pure product in acceptable initial yield in minimal time, the reaction solution can be recycled to make additional product by filtering the solid ester and recharging the filtrate with additional carboxylic acid.

Precipitation of the aryl esters according to the inventive methods, allows for quick and easy purification and isolation of the product ester. The precipitation is driven, in part, by the relatively concentrated nature of the reaction mixture. That is, the inventive methods include a molar ratio of aryl acid to alcohol of 1:100 to 1:5. In certain exemplary embodiments, the ratio is 1:100 to 1:5, including 1:60 to 1:5, including 1:50 to 1:5, including 1:20 to 1:5. This is a departure from conventional techniques in so far as the general intention of organic chemists is to include a much higher amount of solvent (alcohol) to ensure the reaction achieves solution and to drive the reaction to completion.

In certain embodiments, the acid catalyst is provided in an amount sufficient to catalyze the reaction. In certain embodiments the acid catalyst is a strong acid such as, hydrochloric acid, phosphoric acid, nitric acid, sulfuric acid, and the like. In certain embodiments the acid catalyst is sulfuric acid. In certain embodiments, the aryl acid and acid catalyst are added together in a ratio of aryl acid:acid catalyst in a molar ratio of from 1:0.001 to 1:0.05.

The reaction can proceed for any length of time necessary to achieve conversion of the aryl acid to the ultimate aryl ester product. In certain embodiments, the reaction mixture is heated for 1 to 48 hours. In certain embodiments, the reaction mixture is heated for 1 to 24 hours. In certain embodiments, the reaction mixture is heated for 0.5 hours to 10 hours. In certain embodiments, the reaction mixture is heated for 0.5 hours to 6 hours.

Following the esterification process, in certain embodiments, the aryl ester can be crystallized from the reaction mixture by conventional methods known to those in the art. In certain embodiments, the aryl ester crystallizes from the reaction mixture during heating. In certain embodiments, the hot mixture including the aryl ester is filtered through a filter media. In certain embodiments, the hot mixture including the aryl ester is cooled to a temperature of −40° C. to 50° C., −30° C. to 50° C., −20° C. to 50° C., −10° C. to 50° C., 0° C. to 50° C., 0° C. to 30° C., 10° C. to 30° C., or 20° C. to 30° C. Once cooled, the mixture is then filtered through a filter media.

In certain exemplary embodiments, the aryl ester may not directly precipitate from the reaction mixture. In certain embodiments, a second solvent is added to the reaction mixture prior to filtering the reaction mixture. In certain embodiments, water is added to the reaction mixture prior to filtering the reaction mixture. In certain embodiments, water is added in an amount of 10 mL per gram of ester.

Following the crystallization process, the aryl ester can be isolated from the reaction mixture by conventional methods known to those in the art. After isolation, the product can be washed with an organic solvent. In one embodiment, the aryl ester is washed with 0.1 to 10 mL of alcohol per gram of product. In certain embodiments, the aryl ester is washed with methanol.

EXAMPLES

The following paragraphs describe and demonstrate exemplary embodiments of the general inventive concepts and the aryl esters made therefrom. The exemplary embodiments are provided solely for the purpose of illustration and are not to be construed as limitations of the present disclosure, as many variations thereof are possible without departing from the spirit and scope of the present disclosure. The aryl acid esters may be prepared in accordance with the methods described herein.

The reaction conditions provided herein, can be grouped into three categories, as outlined in Tables 1, 2, and 3. Tables 1 and 2 show results for experiments that lead to direct precipitation of pure esters from the cooled reaction solutions. Table 1 shows the conditions and results for reactions wherein the aryl acid has little to no solubility in the alcohol solvent. The refluxing solutions are heterogeneous at the beginning but clarify as the reaction is heated toward reflux. As the solutions cool, pure ester products crystallize and are isolated.

The following is a description of an exemplary reaction according to the reactants in Table 1, methyl 4-bromobenzoate: 10.04 grams of 4-bromobenzoic acid (0.0500 moles) and 30.0 mL of methanol (0.741 moles) were added to a 100-mL round bottom flask. To this heterogeneous mixture was added 2.0 mL concentrated $H_2SO_4$ catalyst and 3 boiling stones. The mixture was brought to reflux and as the reaction proceeded, the heterogeneous solution began to clear. After 90 minutes at reflux, the 4-bromobenzoic acid reactant was completely dissolved. The reaction mixture was refluxed for a total of 3.5 hours. At the end of this time, the flask was removed from the heat and allowed to cool to room temperature. Within 5 minutes of cooling, crystalline ester product began to precipitate from the warm reaction solution. After the flask cooled to room temperature, the reaction mixture was further chilled by placing it in an ice bath for 30 minutes. A large amount of white, crystalline product was observed to have precipitated. It was collected by vacuum filtration, transferred and washed with approximately 50 mL of a chilled 50:50 mixture of water and methanol, and allowed to dry. After drying, 9.567 grams of methyl 4-bromobenzoate product was isolated as a highly pure crystalline solid with a melting point of 76.7-77.8° C., as compared to a literature melting point of 77-81° C. The isolated yield of product was 89%.

TABLE 1

| Carboxylic acid (mass) | Alcohol (volume) | Ester (yield) | Molar Ratio (acid:alcohol) | Time for Dissolution | Rxn Time (reflux) |
|---|---|---|---|---|---|
| 4-bromobenzoic acid (10.0 g) | methanol (30.0 mL) | 89% | 1:15 | 90 minutes | 3.5 hours |
| 4-iodobenzoic acid (1.55 g) | methanol (12.0 mL) | 63% | 1:50 | 60 minutes | 1.5 hours |
| 4-methoxybenzoic acid (9.43 g) | methanol (25.0 mL) | 35% | 1:10 | 90 minutes | 5.0 hours |
| 4-methoxybenzoic acid (12.6 g) | methanol (50.0 mL) | 49% | 1:15 | 45 minutes | 5.0 hours |
| 4-nitrobenzoic acid (4.98 g) | methanol (12.0 mL) | 92% | 1:10 | 3 hours | 6.0 hours |
| 4-nitrobenzoic acid (13.7 g) | methanol (50.0 mL) | 92% | 1:15 | 60 minutes | 5.0 hours |
| 4-chlorocinnnamic acid (29.5 g) | methanol (120 mL) | 87% | 1:20 | 90 minutes | 2.0 hours |
| 4-bromocinnamic acid (3.41 g) | methanol (12.0 mL) | 77% | 1:20 | 75 minutes | 1.5 hours |
| 4-methoxycinnamic acid (14.5 g) | methanol (50.0 mL) | 91% | 1:15 | 45 minutes | 5.0 hours |

TABLE 1-continued

| Carboxylic acid (mass) | Alcohol (volume) | Ester (yield) | Molar Ratio (acid:alcohol) | Time for Dissolution | Rxn Time (reflux) |
|---|---|---|---|---|---|
| 4-nitrocinnamic acid (3.24 g) | methanol (30.0 mL) | 98% | 1:45 | not observed | 4.0 hours |
| 4-nitrobenzoic acid (7.24 g) | ethanol (25.0 mL) | 77% | 1:10 | 45 minutes | 6.0 hours |
| 4-methoxycinnamic acid (15.2 g) | ethanol (50.0 mL) | 80% | 1:10 | 30 minutes | 5.0 hours |
| 4-nitrocinnamic acid (1.39 g) | ethanol (20.0 mL) | 92% | 1:50 | 90 minutes | 3.0 hours |

The following is a description of an exemplary reaction according to the reactants in Table 2, ethyl 4-methoxycinnamate: 3.09 grams of 4-methoxycinnamic acid (0.0174 moles) and 15.0 mL of ethanol (0.258 moles) were added to a 25-mL round bottom flask. To this mixture was added 0.5 mL concentrated $H_2SO_4$ catalyst and 3 boiling stones. The mixture was brought to reflux, and after 20 minutes at reflux the 4-methoxycinnamic acid was completely dissolved. The reaction solution was refluxed for a total of 4.0 hours. At the end of this time, the flask was removed from the heat and allowed to cool to room temperature then further chilled by refrigerating the flask overnight. A large amount of white, crystalline product was observed to have precipitated. It was collected by vacuum filtration, transferred and washed with approximately 20 mL of chilled ethanol, and allowed to dry. After drying, 2.23 grams of ethyl 4-methoxycinnamate product was isolated as a highly pure crystalline solid with a melting point of 47.0-48.2° C., as compared to a literature melting point of 49° C. The isolated yield of product was 63%.

Table 2 shows the results for experiments that have also led to direct precipitation of pure aryl ester products from the cooled reaction solutions. In contrast to Table 1, the solubility of carboxylic acids in Table 2 was higher at the start of reflux.

TABLE 2

| Carboxylic acid (mass) | Alcohol (volume) | Ester (yield) | Molar Ratio (acid:alcohol) | Time for Dissolution | Rxn Time (reflux) |
|---|---|---|---|---|---|
| 3-bromobenzoic acid (4.91 g) | methanol (20.0 mL) | 52% | 1:20 | Immediate | 4.5 hours |
| 3-bromobenzoic acid (9.96 g) | methanol (20.0 mL) | 75% | 1:10 | Immediate | 4.5 hours |
| 3-nitrobenzoic acid (2.52 g) | methanol (12.0 mL) | 43% | 1:20 | 5 minutes | 1.0 hours |
| 3-nitrobenzoic acid (20.8 g) | methanol (50.0 mL) | 86% | 1:10 | 5 minutes | 5.0 hours |
| 4-nitrobenzoic acid (2.53 g) | methanol (12.0 mL) | 57% | 1:20 | 20 minutes | 1.5 hours |
| cinnamic acid (2.25 g) | methanol (12.0 mL) | 8% | 1:20 | Immediate | 30 minutes |
| 4-methylcinnnamic acid (2.44 g) | methanol (12.0 mL) | 41% | 1:20 | 10 minutes | 30 minutes |
| 4-methoxycinnamic acid (22.2 g) | methanol (120 mL) | 81% | 1:25 | 15 minutes | 3.5 hours |
| 3,4,5-trimethoxycinnamic acid (4.71 g) | methanol (12.0 mL) | 85% | 1:15 | Immediate | 4.0 hours |
| 3-nitrobenzoic acid (2.41 g) | ethanol (25.0 mL) | 44% | 1:30 | Immediate | 6.0 hours |
| 3-nitrobenzoic acid (3.80 g) | ethanol (25.0 mL) | 51% | 1:20 | Immediate | 5.0 hours |
| 3-nitrobenzoic acid (7.27 g) | ethanol (25.0 mL) | 72% | 1:10 | Immediate | 6.0 hours |
| 4-nitrobenzoic acid (4.80 g) | ethanol (25.0 mL) | 77% | 1:15 | 20 minutes | 6.0 hours |
| 4-methoxycinnamic acid (3.09 g) | ethanol (15.0 mL) | 63% | 1:15 | 20 minutes | 4.0 hours |
| 3,4,5-trimethoxycinnamic acid (3.28 g) | ethanol (12.0 mL) | 63% | 1:15 | Immediate | 4.0 hours |

The following is a description of an exemplary reaction according to the reactants in Table 3, ethyl 4-hydroxybenzoate: 4.72 grams of 4-hydroxybenzoic acid (0.0342 moles) and 37 mL of ethanol (0.635 moles) were added to a 100-mL round bottom flask. To this homogeneous mixture was added 1.0 mL concentrated $H_2SO_4$ catalyst and 3 boiling stones. The mixture was brought to reflux and heated for 5.5 hours. At the end of this time, the flask was removed from the heat and allowed to cool to room temperature. The reaction solution was transferred to a 125-mL Erlenmeyer flask which was then chilled by placing the flask in an ice bath. Chilled deionized water (80 mL) was slowly added to the reaction flask. As the water was added, white crystalline product began to precipitate. It was collected by vacuum filtration, transferred and washed with approximately 30 mL of chilled water, and allowed to dry. After drying, 4.28 grams of ethyl 4-hydroxybenzoate product was isolated as a highly pure crystalline solid with a melting point of 114.2-115.0° C., as compared to a literature melting point of 114-117° C. The isolated yield of product was 76%.

Table 3 shows the results for reactions where aryl ester product did not directly precipitate from the cooled reactions. For the methyl and ethyl esters of 4-hydroxybenzoic acid, the esters can be precipitated by adding water to the cooled reaction solution.

TABLE 3

| Carboxylic acid (mass) | Alcohol (volume) | Ester (yield) | Molar Ratio (acid:alcohol) | Time for Dissolution | Rxn Time (reflux) |
|---|---|---|---|---|---|
| 4-chlorobenzoic acid (1.03 g) | methanol (12.0 mL) | 11% | 1:50 | 15 minutes | 1.5 hours |
| 4-hydroxybenzoic acid (2.00 g) | methanol (12.0 mL) | 30% | 1:20 | Immediate | 30 minutes |
| 4-hydroxybenzoic acid (4.72 g) | ethanol (37.0 mL) | 76% | 1:20 | Immediate | 5.5 hours |

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present disclosure can comprise, consist of, or consist essentially of the essential elements and limitations of the disclosure as described herein, as well as any additional or optional components, or limitations described herein or otherwise useful in chemical synthesis of aryl esters.

To the extent that the terms "include," "includes," or "including" are used in the specification or the claims, they are intended to be inclusive in a manner similar to the term "comprising" as that term is interpreted when employed as a transitional word in a claim. Furthermore, to the extent that the term "or" is employed (e.g., A or B), it is intended to mean "A or B or both A and B." When the applicants intend to indicate "only A or B but not both," then the term "only A or B but not both" will be employed. Thus, use of the term "or" herein is the inclusive, and not the exclusive use. In the present disclosure, the words "a" or "an" are to be taken to include both the singular and the plural. Conversely, any reference to plural items shall, where appropriate, include the singular.

In some embodiments, it may be possible to utilize the various inventive concepts in combination with one another (e.g., one or more of the exemplary embodiments may be utilized in combination with each other). Additionally, any particular element recited as relating to a particularly disclosed embodiment should be interpreted as available for use with all disclosed embodiments, unless incorporation of the particular element would be contradictory to the express terms of the embodiment. Additional advantages and modifications will be readily apparent to those skilled in the art. Therefore, the disclosure, in its broader aspects, is not limited to the specific details presented therein, the representative apparatus, or the illustrative examples shown and described.

The invention claimed is:
1. A method for the synthesis of an aryl ester of formula II,

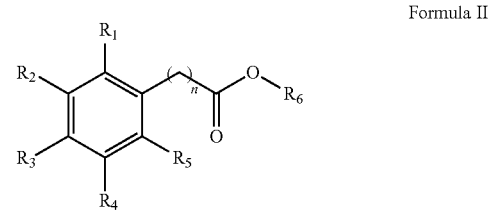

Formula II wherein $R_1$, $R_2$, $R_3$, $R_4$, and $R_5$ each independently represents a hydrogen atom, an alkyl group having from 1 to 6 carbon atoms, a cycloalkyl group having from 3 to 6 carbon atoms, a halogen atom, an alkoxy group having from 1 to 6 carbon atoms, a haloalkyl group having from 1 to 6 carbon atoms, a haloalkoxy group having from 1 to 6 carbon atoms, an alkylthio group having from 1 to 6 carbon atoms, an alkylsulphonyl group having from 1 to 6 carbon atoms, a nitro group, a hydroxy group, a cyano group, an amino group, an alkylamino group having from 1 to 6 carbon atoms or a dialkylamino group having from 1 to 6 carbon atoms in each alkyl part,
wherein n is equal to 0 or to an alkyl group having from 1 to 6 carbon atoms,
wherein $R_6$ represents an alkyl group having from 1 to 6 carbon atoms or a cycloalkyl group having from 3 to 6 carbon atoms,
the method comprises:
mixing an aryl acid according to formula I, with an alcohol solvent and an acid catalyst to form a reaction mixture,

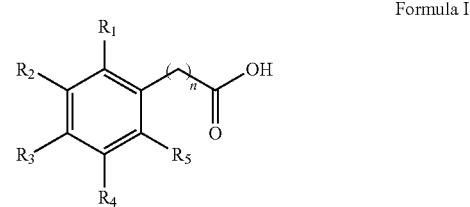

Formula I heating the reaction mixture for a period of 0.5 to 10 hours, filtering the reaction mixture to obtain an aryl ester, and washing the aryl ester with a second solvent, wherein the molar ratio of aryl acid to alcohol solvent is 1:100 to 1:5, and wherein the molar ratio of aryl acid:acid catalyst is from 1:0.5 to 1:0.01.

2. The method of claim 1, wherein the reaction is heated for a period of 0.5 to 6 hours.

3. The method of claim 1, wherein the molar ratio of aryl acid to alcohol is 1:60 to 1:5.

4. The method of claim 1, wherein the molar ratio of aryl acid to alcohol is 1:50 to 1:5.

5. The method of claim 1, wherein the molar ratio of aryl acid to alcohol is 1:20 to 1:5.

6. The method of claim 1, wherein $R_1$, $R_2$, $R_3$, $R_4$, and $R_5$ each independently represents a hydrogen atom, an alkyl group having from 1 to 6 carbon atoms, a cycloalkyl group having from 3 to 6 carbon atoms, a halogen atom, or an alkoxy group having from 1 to 6 carbon atoms.

7. The method of claim 1, wherein n is alkyl group having from 1 to 6 carbon atoms.

8. The method of claim 1, wherein $R_6$ represents an alkyl group having from 1 to 6 carbon atoms.

9. The method of claim 1, wherein the second solvent is selected from water, methanol, ethanol, and mixtures thereof.

10. The method of claim 1, wherein the mixture is cooled prior to filtering.

11. The method of claim 1, wherein the catalyst is a strong acid.

\* \* \* \* \*